United States Patent [19]

Bright

[11] 4,049,719
[45] Sept. 20, 1977

[54] PROCESS FOR PREPARING BIS(HYDROXYMETHYL) METHYLPHOSPHINE OXIDE

[75] Inventor: John Harvey Bright, Kendall Park, N.J.

[73] Assignee: American Cyanamid Company, Stamford, Conn.

[21] Appl. No.: 732,632

[22] Filed: Oct. 15, 1976

Related U.S. Application Data

[63] Continuation-in-part of Ser. No. 567,565, April 14, 1975, abandoned.

[51] Int. Cl.$^2$ .............................................. C07F 9/53
[52] U.S. Cl. ..................... 260/606.5 P; 260/606.5 F
[58] Field of Search ................................ 260/606.5 P

[56] References Cited

U.S. PATENT DOCUMENTS

| | | | |
|---|---|---|---|
| 3,716,580 | 2/1973 | Maier | 260/606.5 P |
| 3,732,316 | 5/1973 | Lin | 260/606.5 P |

OTHER PUBLICATIONS

Trippett, J. Chem. Soc., 1961, pp. 2813–2816.

*Primary Examiner*—Arthur P. Demers
*Attorney, Agent, or Firm*—Charles J. Fickey

[57] ABSTRACT

A process is provided for preparing bis(hydroxymethyl)methylphosphine oxide, comprising (1) thermally rearranging tris(hydroxymethyl)phosphine at elevated temperatures in the presence of a catalytic amount of a strong, non-oxidizing acid, having an ionization constant greater than $10^{-3}$, or a source thereof, to obtain the desired bis(hydroxymethyl)methylphosphine oxide, and (2) recovering the latter compound from the reaction mixture.

10 Claims, No Drawings

PROCESS FOR PREPARING BIS(HYDROXYMETHYL) METHYLPHOSPHINE OXIDE

This application is a continuation-in-part of Ser. No. 567,565, filed Apr. 14, 1975, and now abandoned.

BACKGROUND OF THE INVENTION

This invention relates to a process for preparing bis(-hydroxymethyl)methylphosphine oxide.

Tris(hydroxymethyl) phosphine (THP) is a hazardous material because of its lability which sometimes leads to expolsions on heating at high temperatures without a solvent. The heating of crude THP at high temperatures is particularly hazardous.

The preparation of bis(hydroxymethyl)methylphosphine oxide by thermally rearranging tris(hydroxymethyl) phosphine in the presence of a solvent such as dimethyl sulfoxide, acetic acid, N-methyl pyrrolidone, N,N-dimethylforamide, and the like, at elevated temperatures, as disclosed by Lin in U.S. Pat. No. 3,732,316, moderates the aforementioned hazard.

In the process of Lin (see Example 1) 40% of the final product composition is tris(hydroxymethyl) phosphine oxide (THPO) when solvent used is dimethyl sulfoxide. When acetic acid is used as the solvent the product is a mixture of various phosphorous compounds containing acetate groups. When N-methyl pyrrolidone is used as the solvent the product composition is 78-79% of bis(-hydroxymethyl)methylphosphine oxide and between 21-22% of the THPO.

Thus, there is a need for an improved process which moderates the hazardous lability of tris(hydroxymethyl) phosphine and produces a product having a significantly higher percentage of bis(hydroxymethyl)methylphosphine oxide.

Accordingly, it is an object of the present invention to provide an improved process for preparing bis(hydroxymethyl) -methylphosphine oxide by thermally rearranging tris(hydroxymethyl)phosphine.

It is a further object of this invention to provide an improved process for preparing bis(hydroxymethyl)methylphosphine oxide by thermally rearranging tris(hydroxymethyl)phosphine in an inert solvent.

Additional objects and advantages of the invention will be set forth in part in the description which follows, and in part will be obvious from the description, or may be realized by practice of the invention, the objects and advantages being realized and attained by means of the methods, processes, instrumentalities and combinations particularly pointed out in the appended claims.

SUMMARY OF THE INVENTION

It has been discovered that the foregoing objects may be achieved by an improved process which comprises heating tris(hydroxymethyl)phosphine and a catalytic amount of a strong, non-oxidizing acid, or source of said acid, at elevated temperatures to form the desired bis(-hydroxymethyl)methylphosphine oxide and recovering the latter compound.

More particularly, it has been discovered that the foregoing objects are preferably achieved by heating a solution of tris(hydroxymethyl) phosphine in an inert solvent containing a catalytic amount of a strong, non-oxidizing acid, or source of said acid at elevated temperatures and recovering the desired bis(hydroxymethyl)-methylphosphine oxide therefrom.

It is to be understood that both the foregoing general description and the following detailed description are exemplary and explanatory and are not restrictive of the invention.

The bis(hydroxymethyl)methylphosphine oxide which is provided in improved quality and yield by the advent of this invention finds utility as a flame retardant for synthetic polymers, particularly polyurethanes and polyesters.

DESCRIPTION OF THE PREFERRED EMBODIMENT

This invention pertains to an improved process for preparing bis(hydroxymethyl)methylphosphine oxide by heating tris(hydroxymethyl)phosphine, preferably in an inert solvent in the presence of 0.75 to 8.0 percent mole of a catalyst which is a strong non-oxidizing acid having an ionization constant greater than $1 \times 10^3$, or a source thereof, preferably 0.75 to 2.0 mole percent of methanesulfonic acid, at a temperature from about 100° to about 190° C., preferably at a temperature from about 115° to about 140° C., for a period from about 15 to about 80 hours, preferably from about 20 to about 40 hours, with the higher temperature in each range requiring the shorter heating period, and recovering the product therefrom.

While the process of this invention can be effected by heating the THP neat in the presence of a strong non-oxidizing acid alone or a source thereof, it is preferable to carry out the reaction in the further presence of an alcoholic solvent; methyl cellosolve is a preferred solvent.

Illustrative of the strong non-oxidizing acids, which may be used in the process of this invention are hydrochloric acid, hydrobromic acid, hydroiodic acid, phosphoric acid ($K_1 = 7.5 \times 10^{-3}$), trichloroacetic acid ($K = 1.3 \times 10^{-1}$), oxalic acid ($K_1 = 6.5 \times 10^{-1}$), sulfonic acids, such as p-toluene sulfonic acid, phenylsulfonic acid ($K = 2.8 \times 10^{-3}$), α-napthalene sulfonic acid ($K = 6.8 \times 10^{-1}$), methanesulfonic acid, and the like. Strong oxidizing acids such as sulfuric, nitric, and chloric acid are not useful.

Sources of such acids include tetrakis (hydroxymethyl)phosphonium chloride, tetrakis (hydroxymethyl) phosphonium phosphate, and tetrakis (hydroxymethyl) phosphonium oxalate.

It is critical that the crude tris(hydroxymethyl) -phosphine starting material be essentially neutral, that is a 50 percent aqueous solution of this material should have a pH no higher than 6.9-7.0. If the pH of the starting material is slightly above 7.0, the pH should be adjusted to pH 6.9-7.0 by addition of an acid thereto. In the case of crude THP the amount of acid required to adjust the pH to 6.9-7.0 may vary depending on amount of impurities present.

The following examples are illustrative of the process of this invention, and will enable persons skilled in the art to better understand and practice the invention.

EXAMPLE 1

To 22.0 g. of crude tris(hydroxymethyl)phosphine (90% real, 0.158 mole; 5% water, 4% THPO, 0.5% formaldehyde) in a suitable reaction vessel is added 50 mls of deaerated toluene and the mixture is azeotroped under nitrogen to remove water and then concentrated under vacuum to remove all but 2 mls. of the toluene. To the reaction mixture are added 18 mls. of nitrogen-deearated methyl cellosolve and 0.11 g. (0.0012 mole;

0.75 mole percent based on the THP) of methanesulfonic acid. The reaction mixture is then refluxed (134°-135° C) under nitrogen for 23 hours and cooled to room temperature. A sample is removed and labeled A. The reaction mixture is then heated at 134°-135° C for an additional 18 hours and cooled to room temperature. Another sample is removed and labeled B.

The analytical results obtained by hydrogen, nuclear magnetic resonance analysis of these samples are reported in Table I as mole percent of the original real THP.

TABLE I

| Sample | $CH_3\overset{O}{\overset{\|}{P}}(CH_2OH)_2$ | THPO | Phosphonium Salts |
|---|---|---|---|
| | | Mole % | |
| A | 91 | 5 | 4 |
| B | 92 | 5 | 3 |

EXAMPLE 2

The following example illustrates the process of this invention carried out in methyl cellosolve with 2 mole percent of acid.

To 14.0 g. of crude tris(hydroxymethyl)phosphine (90% real, 0.100 mole) in 11 mls. of nitrogen-deaereated methyl cellosolve in a suitable reaction vessel is added 0.16 g. (0.0017 mole; 1.7 mole percent based on THP) of methanesulfonic acid and the reaction mixture is heated at 128°-130° C for a period of 23 hours under a nitrogen atmosphere. The reaction mixture is then cooled to room temperature. Analysis of the reaction mixture shows that 79% of the original THP is rearranged to bis(hydroxymethyl)methylphosphine oxide.

EXAMPLE 3

This example shows that the mole percent of THP rearranged to dihydroxymethyl phosphine oxide is significantly lowered if an acid catalyst is not included.

To 8.7 g. of methyl cellosolve which has been deaerated with nitrogen is added 11.4 g. of crude tris(hydroxymethyl)phosphine (79% real, 0.072 mole) which also contains 16% THPO and about 5% water. The mixture is stirred to dissolve the THP and 0.15 g. of dimethylaniline is added thereto to neutralize* any acid which may be present. The mixture is then heated at reflux (131°-134° C) for 23 hours under nitrogen. The reaction mixture is cooled to room temperature and a sample is removed for analysis and labeled A. The reaction mixture is then refluxed at 131°-134° C for an additional 18 hours and cooled to room temperature. A second sample is then removed for analysis and labeled B.
*Dimethylaniline is added until a 50% solution of the reaction mixture in water has a pH of 7.

The analytical results obtained by 31 P nuclear resonance analysis are reported in Table II as mole percent based on the orignial THP present.

TABLE II

| Sample | $CH_3\overset{O}{\overset{\|}{P}}(CH_2OH)_2$ | THPO | THP |
|---|---|---|---|
| | | Mole % | |
| A | 64 | 18 | 18 |
| B | 75 | 21 | 4 |

EXAMPLE 4

This example illustrates a rearrangement of THP (neat) without an acid catalyst.

A sample of 9.6 g. (0.077 mole) of tris(hydroxymethyl)phosphine is heated under a nitrogen atmosphere for 8 ¼ hours at 116°-122° C while stirring slowly. At the end of this period the reaction mixture is cooled to room temperature and a sample is analyzed by hydrogen nuclear magnetic resonance. Analysis shows that only 9 mole percent of the original THP has rearranged to

$$CH_3\overset{O}{\overset{\|}{P}}(CH_2OH)_2.$$

EXAMPLE 5

This example illustrates the process whereby THP (neat) is heated for a relatively short period with hydrochloric acid.

A mixture of 10.7 g. (0.086 mole) of tris(hydroxymethyl)phosphine and 0.17 g. (0.0017 mole, 1.97 mole percent) of concentrated hydrochloric acid is heated under a nitrogen atmosphere at 120°-125° C while stirring slowly for 6 ½ hours. Hydrogen nuclear magnetic analysis of the reaction mixture after this period shows that 35 mole percent of the original THP has been converted to bis(hydroxymethyl)methylphosphine oxide.

EXAMPLE 6

This example illustrates the process carried out with THP(neat) and hydrochloric acid.

A mixture of 8.0 g. (0.064 mole) of tris(hydroxymethyl)phosphine and 0.20 g. (0.002 mole, 3.1 mole percent) of concentrated hydrochloric acid is heated under a nitrogen atmosphere while stirring at 119°-120° C for 15 hours. The temperature is then raised to 126°-127° C for 6 hours at which point the heating is discontinued and the mixture is cooled to 30° C. A small sample (A) is removed and 0.12 g. (0.001 mole, 1.6 mole percent) of concentrated hydrochloric acid is added to the reaction mixture. Heating is resumed under nitrogen at 126°-127° C for an additional 16 hours after which the reaction mixture is cooled to room temperature and a second sample (B) is removed. Both samples are then analyzed by hydrogen nuclear magnetic resonance; the results obtained are reported in Table III as mole percent of the THP present originally.

TABLE III

| Sample | $CH_3-\overset{O}{\overset{\|}{P}}(CH_2OH)_2$ | Phosphonium Salts | THP |
|---|---|---|---|
| | | Mole % | |
| A | 65 | 7 | 28 |
| B | 89 | 8 | none detected |

EXAMPLE 7

The following example illustrates the process carried out in THP (neat) with tetrakis(hydroxymethyl)phosphonium chloride as the catalyst.

A mixture of 9.9 g. (0.079 mole) of tris(hydroxymethyl)phosphine and 1.05 g. (0.006 mole; 7.6 mole percent based on THP) of tetrakis(hydroxymethyl)phosphonium chloride is heated under a nitrogen atmosphere at 111°-115° C while stirring slowly for 24½ hours. The reaction mixture is then cooled to room temperature and analyzed by "hydrogen nuclear magnetic resonance." The analysis shows that 77 mole percent of the THP has rearranged to bis(hydroxymethyl)-methylphosphine oxide.

I claim:

1. In a process for preparing bis(hydroxymethyl)-methylphosphine oxide which comprises heating tris(hydroxymethyl) phosphine to rearrange said tris(hydroxymethyl)phosphine to bis(hydroxymethyl)methylphosphine oxide, the improvement which comprises adding a catalytic amount of a strong non-oxidizing acid, having an ionization constant greater than $10^{-3}$, or a source of a catalytic amount of said acid, thereto before heating.

2. The process of claim 1 wherein said heating is carried our at from about 100° to about 190° C.

3. The process of claim 1 wherein the amount of acid is from about 0.75 to 8 mole percent based on said tris(hydroxymethyl)phosphine.

4. The process of claim 1 wherein said heating is for a period of about 15 to 80 hours.

5. The process of claim 1 wherein the process is carried out in the presence of an alcoholic solvent.

6. The process of claim 1 wherein the tris(hydroxymethyl) phosphine starting material has an essentially neutral pH.

7. The process of claim 6 wherein said starting material is treated to obtain a pH of about 6.9 to 7 prior to initiation of the process.

8. The process of claim 1 wherein the tris(hydroxymethyl) phosphine is heated at a temperature from about 110° C. to about 130° C. for a period of about 20 to 40 hours in the presence of about 3 to 8 mole percent of a hydrochloric acid, or a source of hydrochloric acid, based on the tris(hydroxymethyl) phosphine.

9. The process of claim 1 wherein the tris(hydroxymethyl)phosphine is heated in methyl cellosolve at a temperature of about 130°-135° C for a period of about 24 to about 40 hours in the presence of 0.75 to 1.77 mole percent of methanesulfonic acid, based on the tris(hydroxymethyl) phosphine.

10. The process of claim 8 wherein the source of hydrochloric acid is tetrakis(hydroxymethyl)phosphonium chloride.

* * * * *